United States Patent [19]
Reddel et al.

[11] Patent Number: 4,885,238
[45] Date of Patent: Dec. 5, 1989

[54] IMMORTALIZED HUMAN BRONCHIAL EPITHERIAL MESOTHELIAL CELL LINES

[75] Inventors: Roger R. Reddel, Kensington; Ke Yang; Johng S. Rhim, both of Bethesda, all of Md.; Douglas Brash, Washington, D.C.; Robert T. Su, Lawrence, Kans.; John F. Lechner, Kensington, Md.; Brenda I. Gerwin; Curtis C. Harris, both of Bethesda, Md.; Paul Amstad, Epolinges, Switzerland

[73] Assignee: The United States of America as represented by the Department of Health and Human Services, Washington, D.C.

[21] Appl. No.: 114,508

[22] Filed: Oct. 30, 1987

[51] Int. Cl.[4] .................. C12Q 1/18; C12Q 1/02; C12Q 1/68; C12N 15/00
[52] U.S. Cl. ............................. 435/29; 435/6; 435/32; 435/172.1; 435/240.2; 435/240.31; 435/948; 935/52; 935/57
[58] Field of Search .............. 435/29, 170, 5, 30, 435/32, 240.1, 240.2, 172.1, 948, 67; 935/52, 57

[56] References Cited
PUBLICATIONS

Lechner et al, Cancer Research, vol. 43, Dec. 1983, pp. 5915–5921.
Yoakum et al, Science, vol. 227, Mar. 1985, pp. 1174–1179.
*Molecular and Cellular Biology* (1987), 7:2031–2034, Brash et al.
*Federation Proceedings* (1987), 46:718, Nakagawa et al.
*J. Cell. Biochem* (1987), Supplement 11, Lechner et al.
Abstract No. 240, *Proceedings of the American Association for Cancer Research*, 28:60 (1987), Lechner et al.
Abstract No. 469, *Proceedings of the American Association for Cancer Research*, 28:118 (1987), Reddel et al.
Abstract No. 475, *Proceedings of the American Association for Cancer Research*, 28:120 (1987), Rhim et al.
Abstract No. M59, *European Association for Cancer Research* (Jun. 1987), Gerwin et al.
Abstract No. M95, *European Association for Cancer Research* (Jun. 1987), Reddel et al.
Abstract No. 94, *J. Cell Biol.*, 103:27a (1986), Reddel et al.
Abstract No. 95, *J. Cell Biol.*, 103:27a (1986), Ke et al.

*Primary Examiner*—Robert J. Warden
*Assistant Examiner*—Florina B. Hoffer
*Attorney, Agent, or Firm*—Fleit, Jacobson, Cohn, Price Holman & Stern

[57] ABSTRACT

Immortalized human bronchial epithelial and human mesothelial cell lines have been obtained. Various uses of these cell lines have been described.

12 Claims, No Drawings

IMMORTALIZED HUMAN BRONCHIAL EPITHERIAL MESOTHELIAL CELL LINES

BACKGROUND OF THE INVENTION

The present invention is related to immortalized cell-lines. More particularly, the present invention is related to immortalized human bronchial epithelial and human mesothelial cell lines or cell lines derived therefrom.

Lung cancer is one of the more common forms of cancer and the cell type in which the majority of these cancers arise is the bronchial epithelial cells. Mesothelial cells are a less common, but important, site of origin of lung cancer. Both, normal human bronchial epithelial cells and normal human mesothelial cells could be cultured in vitro, but only for a limited period of time before cellular replication ceases. When transformed by transfection of the viral Harvey ras oncogene (Yoakum, et al., Science 227:1174, 1985), human bronchial epithelial cells replicate for longer periods of time, but these cells are tumorigenic, grow in serum-containing media as do carcinoma cell lines, and have been constructed to contain an oncogene closely related to oncogenes sometimes found in human carcinomas. Similarly, human bronchial carcinoma cell lines and mesothelioma cell lines are tumorigenic Clearly, such tumorigenic cell lines are undesirable, inter alia. for carcinogenic studies.

SUMMARY OF INVENTION

It is, therefore, an object of the present invention to provide non-tumorigenic human cell lines of bronchial epithelial and of mesothelial cell origin with unlimited proliferative potential and capable of growing in the same serum-free media as their normal counterpart cells, and which do not contain an oncogene found in naturally occurring tumors.

Other objects and advantages of the present invention would become apparent from the Detailed Description of Invention.

DETAILED DESCRIPTION OF INVENTION

The above and other objects and advantages of the present invention are achieved by non-tumorigenic, human bronchial epithelial cell lines continually growing when cultured in vitro in suitable growth medium.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "immortalized" as used herein means that the cell line grows continually without senescence when cultured in vitro in a suitable growth medium.

General Method for Construction of Cell Lines

Normal human bronchial epithelial (NHBE) cells were cultured from explants of necropsy tracheobronchial specimens from noncancerous individuals as described by Lechner, et al.,: J. Tissue Culture Methods 9:43–48, 1985. Normal human mesothelial (NHM) cells were cultured from pleural effusions or ascites fluids as described by Lechner et al., (Proc. Natl. Acad. Sci. U.S.A. 82:3884–3888, 1985). The cells were infected with SV40 virus or with adenovirus-12 SV40 hybrid virus, or transfected with a recombinant plasmid containing the Rous sarcoma virus long terminal repeat and the ori-SV40 early region by strontium phosphate coprecipitation (Brash, et al.: Molec. Cell. Biol., 1987). Colonies of cells transformed by each of these three methods were easily recognizable morphologically using phase contrast microscopy and were individually trypsinized and serially passaged. In all cases the lifespan of these cultures was extended compared to NHBE or NHM; most of the cultures underwent a prolonged period of senescence referred to as "crisis". With continued culture, in some cases colonies of cells which had escaped senescence arose; such surviving colonies were subsequently passaged for extended period of time and showed unlimited growth potential. Like NHBE cells, but unlike bronchial carcinoma cells, some of the cell lines thus derived retained the capacity to undergo squamous differentiation in response to serum exposure. Injection of these cells into irradiated athymic nude mice did not result in formation of tumors after periods of up to nine months. Furthermore, these cell lines were found to be suitable recipients for transfection of additional oncogenes and useful for testing the cytotoxicity potential of chemical and physical agents, the growth inhibition or promoting capability of biological agents, and squamous differentiating potential of chemical and biological agents.

EXAMPLE 1

Development of BES-1A1.6 Cell Line

Normal human bronchial epithelial (NHBE) cells were cultured from explants of autopsy specimens from noncancerous individuals as described by Lechner, et al.: J. Tissue Culture Methods 9: 43–48,1985. The cells were cultured in a serum-free medium, LHC-9, consisting of LHC basal nutrient medium with calcium 0.08 mM, L-glutamine 1 mM, trace elements, gentamicin 50 $\mu$g/ml, insulin 5 $\mu$g/ml, transferrin 10 $\mu$g/ml, hydrocortisone 200 nM, epidermal growth factor 5 ng/ml, phosphoethanolamine 0.5 $\mu$M, ethanolamine 0.5 $\mu$M, epinephrine 0.5 $\mu$g/ml, retinoic acid 0.33 nM, triiodothyronine 10 nM, and bovine pituitary extract (Lechner, et al., supra). In the initial stages of the development of this cell line LHC-8 medium which contains the ingredients listed for LHC-9, with the exception of epinephrine and retinoic acid, was used.

NHBE cells were harvested by trypsinization and seeded in 10 ml growth medium into 100 mm culture dishes (Lux, Miles Scientific, Naperville, Ill.) whose growth surfaces had been coated with a solution of bovine serum albumin, fibronectin and collagen (Lechner, et al. supra).

SV40 virus was prepared in CV-1 cells as described by Su, et al.: J. Virol. 28: 53–65, 1978. NHBE cells were exposed at 37° C. for 90 min. at a multiplicity of infection of approximately 1. The cells were subcultured twice in LHC-8 medium, and exposed to 1% fetal calf serum (FCS) in LHC-8 medium for 47 days. Sixty-one days after infection three colonies of transformed cells were individually subcultured by trypsinization. All subsequent culture of these cells was in serum-free LHC-8 medium. The cell strains thus derived were designated as BES-1A. Two of these strains (BES-1A1 and BES-1A2) were subcloned by limiting dilution.

All of these clonal isolates continued to proliferate for about 18 weeks at which time the cultures senesced (i.e., entered culture "crisis"). After a further period of 11 weeks, proliferating cells appeared in a subcloned culture designated BES-1A1.6. From these cells a line was established which remains in culture more than one year from the time of the initial SV40 infection. These cells are non-tumorigenic.

The BES-1A1.6 line has the special property of being resistant to the squamous differentiation-inducing effects of serum. Whereas NHBE cells are able to be induced to undergo squamous differentiation when exposed to serum, bronchial carcinomas are resistant to this effect (Lechner et al., Cancer Res. 43:5915–5921, 1983). TBE cells lines (human bronchial epithelial cells transformed by the v-Ha-ras oncogene are tumorigenic and are resistant to this effect of serum. The non-tumorigenic BES-1A1.6 cell line is, therefore, intermediate between normal and fully malignant bronchial epithelial cells in this respect.

EXAMPLE 2

Development of the BEAS-2B Cell Line

NHBE cells were cultured from explants of autopsy specimens from noncancerous individuals as described by Lechner, et al., supra. The cells were cultured in a serum-free medium, LHC-9, harvested by trypsinization and seeded in 10 ml growth medium into 100 mm culture dishes (Lux, Miles Scientific, Naperville, Ill.) whose growth surfaces had been coated with a solution of bovine serum albumin, fibronectin and collagen (Lechner, et al., supra).

Adenovirus 12-SV40 (Ad12SV40) hybrid virus (Schell, et al. Proc. Natl. Acad. Sci. U.S.A. 55:81–88, 1966) was grown in Vero cells as described by Rhim, et al.: Proc. Natl. Sci, U.S.A. 78: 313–317, 1981. NHBE cells were exposed to the virus at 37° C. for four hours at a multiplicity of infection of approximately 100. When the cultures reached confluence, each dish was subcultured into two 75 cm$^2$ flasks, the cells were allowed to reach confluence again and then were re-fed twice weekly until transformed colonies appeared and the normal cells senesced. Senescence of the normal cells was accelerated by exposing the cultures to 1% FCS in LHC-9 for 28 days (Lechner, et al.: Differentiation 25: 229–237, 1984); all subsequent culture of these cells was in serum-free LHC-9 medium. Individual colonies were subcultured 41 days after the viral infection and cell strains thus derived from this experiment were designated BEAS-2.

One of the clonal cultures thus derived, BEAS-2B, has proliferated continuously for more than a year and appears to be permanently established. Cells from this cell line injected as passage 18 into athymic nude mice have not formed tumors after one year. This cell line retains the ability to undergo squamous differentiation in response to serum; of the cell lines developed BEAS-2B was the most sensitive to this effect and is thus particularly useful for studies of differentiation-inducing agents. It is able to form an epithelium in de-epithelialized rat tracheas implanted subcutaneously in athymic nude mice and is thus particularly suitable for in vivo studies, especially of chemical carcinogenesis. In assays of invasiveness using matrigel coated filters and Boyden chambers (Albini et al., Cancer 47:3239, 1987) BEAS-2B cells were similar to NHBE cells and 100 times less invasive than TBE-1 cells.

EXAMPLE 3

Development of the BET-b 1A Cell Line

NHBE cells were cultured from explants of autopsy specimens from noncancerous individuals as described by Lechner, et al., 1985, supra. The cells were cultured in a serum-free medium, LHC-9, harvested by trypsinization and seeded in 10 ml growth medium into 100 mm culture dishes (Lux, Miles Scientific, Naperville, Ill.) whose growth surfaces had been coated with a solution of bovine serum albumin, fibronectin and collagen (Lechner, et al., 1985, supra).

The cells were transfected with a plasmid, pRSV-T (obtained from National Cancer Institute), which is an SV40 ori- construct containing the SV40 early region genes and the Rous sarcoma virus long terminal repeat (LTR).

Transfection was by DNA strontium phosphate co-precipitation as described by Brash, et al., Molec. Cell Biol. 7: 2031–2034, 1987. $5 \times 10^5$ NHBE cells plated in 100 mm dishes were transfected with 10 μg DNA precipitated at pH 7.8. The cells were exposed to the precipitate for 4 hr before glycerol shock (Brash, et al., supra). Three days after transfection the cells were passaged; thereafter the cell culture medium was changed twice weekly until subculturing of transformed colonies. Upon confluence the cells were passaged a second time, and senescence of normal cells was hastened by exposure to LHC-9 medium with 1% FCS for 46 days. One colony only was subcultured at day 61 after transfection. All subsequent culture of these cells was in serum-free LHC-9 medium, and the cell strain thus obtained was designated BET1A.

These cells continued to proliferate for about 16 weeks at which time the culture senesced (i.e., entered "crisis"). After a further 13 weeks, colonies of dividing cells appeared from which a cell line has become established; BET1A cells have been in culture for more than a year from the time of initial transfection. These cells are non-tumorigenic, and retain the ability to undergo squamous differentiation in response to serum.

EXAMPLE 4

Development of the BET-2A Cell Line

NHBE cells were cultured from explants of autopsy specimens from noncancerous individuals as described previously herein above. The cells were cultured in a serum-free medium, LHC-9, harvested by trypsinization and seeded in 10 ml growth medium into 100 mm culture dishes (Lux, Miles Scientific, Naperville, Ill.) whose growth surfaces had been coated with a solution of bovine serum albumin, fibronectin and collagen (Lechner, et al., 1985, supra).

The cells were transfected with a plasmid, pRSV-T, (obtained from National Cancer Institute) which is an SV40 ori- construct containing the SV40 early region genes and the Rous sarcoma virus long terminal repeat (LTR).

Transfection was by DNA strontium phosphate co-precipitation as described previously (Brash, et al., supra). $5 \times 10^5$ NHBE cells plated in 100 mm dishes were transfected with 10 μg DNA precipitated at pH 7.8. The cells were exposed to the precipitate for 4 hr before glycerol shock (Brash et al. supra). Three days after transfection the cells were passaged. Thereafter, the cell culture medium was changed twice weekly. Three transformed colonies were subcultured individually at 28 days following transfection, and the clonal cell strains thus derived continued to proliferate in culture for 11 weeks after which time the cultures senesced (i.e. entered "crisis"). After a further 36 weeks, colonies of dividing cells appeared in culture BET-2A from which a cell line has become established; BET-2A cells have been in culture for more than a year from the time of initial transfection. The BET-2A cell line, like the BES-1A1.6 cell line, appears to be resistant to the squamous differentiation-inducing effects of serum. Whereas NHBE cells are able to be induced to undergo squamous differentiation when exposed to serum, bronchial carcinomas are resistant to this effect (Lechner et al., *Cancer Res.* 43:5915-5921, 1983). TBE cell lines (human bronchial epithelial cells transformed by the v-Ha-ras oncogene) are tumorigenic and are resistant to this effect of serum. The non-tumorigenic BET-2A cell line is, therefore, intermediate between normal and fully malignant bronchial epithelial cells in this respect.

EXAMPLE 5

Development of MeT-5A Cell Line

Human mesothelial cells were cultured as described by Lechner, et al.: Proc. Natl. Acad. Sci. U.S.A. 82: 3884-3888, 1985, and were transformed at a frequency of $2 \times 10^{-4}$ by transfection using strontium phosphate coprecipitation (Brash, et al., supra) of a recombinant plasmid, pRSV-T, containing the SV40 virus early region. Colonies of cells transformed by the plasmid, pRSV-T, were isolated and propagated by serial passaging for periods of up to 140 days and 60-70 population doublings from the time of transfection, before cellular senescence occurred. This contrasts with the usual culture lifespan of normal mesothelial cells of 30 days and 15 population doublings. Colonies of dividing cells arose from one such senescent culture, and from these colonies an immortalized cell line, MeT-5A, has been established by continued passaging. This cell line is non-tumorigenic. Although it has been maintained routinely in the serum-containing LHC-MM medium, it also grows well in a serum-free medium.

EXAMPLE 6

Development of BBM Cell Line

BEAS-2B cells were transfected via strontium phosphate co-precipitation (Brash, D. E. et al., Molec. Cell Biol. 7:2031-2034, 1987) with a recombinant plasmid, B-myc/pSV2neo, which had been constructed by ligating a BamH1/EcoR1 fragment of the c-myc gene from the Burkitt's lymphoma cell line CA46 (Showe et al., *Mol. Cell Biol.* 5:501-509, 1985) to a BamH1/EcoR1 fragment of the pSV2neo vector (Southern et al., *Mol. Appl. Genet.* 1:327-341, 1982). BEAS-2B cells so transfected were selected in LCH-9 medium with G418 (Geneticin), and colonies resistant to G418 were isolated individually and subcultured. The cell line arising from one such colony has been designated BBM.

EXAMPLE 7

Development of BZR Cell Line

This cell line has been derived by infecting the BEAS-2B cell line with a recombinant containing the viral Harvey-ras (v-Ha-ras) oncogene. The cell line so derived is highly tumorigenic in athymic nude mice.

The details of the construction are as follows. Zip-neo-v-Ha-ras recombinant retrovirus was constructed by recombining the pZipNeoSV(X) retrovirus (Cepko et al., *Cell* 37:1053-1062, 1984) at its unique Bam H1 restriction enzyme site with a Bam H1 -linkered 1.3 Kb fragment of the H1 clone (Ellis et al., *J. Virol.* 6;408-420, 1980) containing the v-Ha-ras oncogene. Recombinant DNA molecules containing the v-Ha-ras DNA in sense orientation with respect to the pZipNeoSV(X) retrovirus 5' long terminal repeat, were identified by standard DNA manipulation techniques and were used to transfect the psi$^2$ packaging mutant cell line (Mann et al., *Cell* 33:153-159, 1983). Supernatants from these cells were shown to contain infectious retrovirus, and were used to infect the amphotrophic packaging mutant cell line, psiAM (Cone et al., *Proc. Natl. Acad. Sci. U.S.A.* 81:6349-6353 1984). Supernants from this cell line were titered and used to infect BEAS-2B cells.

Following infection of BEAS-2B cells with this virus, G418 resistant cells were selected (Southern et al., *J. Mol. Appl. Genet.* 1:327-341, 1982) and serially subcultured; the cell line so derived was designated BZR. This cell line is highly tumorigenic, forming tumors with a latency period of 2 weeks in 12/15 athymic nude mice each injected with $5 \times 10^6$ cells subcutaneously.

A deposit of the cell lines of the present invention has been made at the ATCC, Rockville, Md., on June 12, 1987 and July 14, 1987 under the accession numbers CRL 9608, 9609, 9442, 9443, 9444, 9482 and 9483, corresponding to cell lines BES-1A1.6, BEAS-2B, BET1A, BET-2A, MeT-5A, BBM and BZR, respectively. The deposits shall be viably maintained, replacing if it became non-viable, for a period of 30 years from the date of the deposit, or for 5 years from the last date of request for a sample of the deposit, whichever is longer and made available to the public without restriction in accordance with the provisions of the law. The Commissioner of Patents and Trademarks, upon request, shall have access to the deposit.

UTILITY OF CELL LINES (1) Identification of potential chemotherapeutic drugs: These cells are useful for screening chemicals suitable for the treatment of cancer and related diseases, by growing them in vitro in medium containing the chemical to be tested and then, after a suitable period of exposure, determining whether and to what extent cytotoxicity has occurred, e.g. by trypan blue exclusion assay or related assays (Paterson, *Methods Enzymol.* 58:141, 1979), or by growth assays such as colony forming efficiency (MacDonald et al., *Exp. Cell. Res.* 50: 417, 1968), all of which are standard techniques well known in the art.

(2) Studies of the control of squamous differentiation, and identification of chemical and biological agents which induce squamous differentiation: This is accomplished by assays previously described for normal human bronchial epithelial cells (Masui, *Proc. Natl. Acad. Sci. U.S.A.*. 83:2438, 1986). As noted in the cell line specification, some retain ability to undergo squamous differentiation in response to serum. Induction of terminal differentiation may be an effective way of controlling the growth of cancer. Chemical and biological substances are screened for their ability to induce differentiation by adding them to the growth medium of these cells and then after a suitable time interval determining whether a complex of changes including cessation of DNA synthesis and the appearance of squamous morphology has occured. The cells are also useful for studies of the biological mechanisms of squamous differentiation, and the existence of both serum-resistant and serum-sensitive cell lines enables comparisons and identification of genes of their protein products involved in the process of differentiation.

(3) Studies of metabolism of caroinogens and other xenobiotics: Carcinogens and other xenobiotics may be added to the growth medium of these cells and then the appearance of metabolic products of these compounds may be monitored by techniques such as thin layer chromatography or high performance liquid chromatography and the like, and the interaction of the compounds and/or their metabolites with DNA is determined.

(4) Studies of DNA mutagenesis: Substances known or suspected to be mutagens may be added to the growth medium of the cells and then mutations may be assayed, e.g., by detection of the appearance of drug resistant mutant cell colonies (Thompson, *Methods Enzymol.* 58:308, 1979). Similarly, cell-mediated DNA mutagenesis, by cocultivating the cells with cell types known or suspected to be capable of secreting mutagenic compounds (Hsu et al., *Proc. Natl. Acad. Sci. U.S.A.* 75:2003, 1978).

(5) Studies of chromosome damaging agents: Substances known or suspected to cause chromosomal damage may be added to the culture medium of these cell lines, and then the extent of chromosomal damage may be measured by techniques such as measurement of the frequency of sister chromatid exchange (Latt et al., In: Tice, R. R. and Hollaender, A., *Sister Chromatid Exchanges.* New York: Plenum Press, pp. 11 ff., 1984).

(6) Studies of malignant transformation by chemical, physical and viral agents, and transferred genes including oncogenes and high molecular weight genomic DNA from tumors, using standard assays such as anchorage independent growth or tumor formation in athymic nude mice. For example, a cloned cellular oncogene from a human tumor has been transferred into the BEAS-2B cell line; the cell line thus derived is BBM. This cell line has been shown to be resistant to the squamous differentiation inducing effects of serum. In a second example, a cloned viral oncogene, v-Ha-ras, has been introduced into the BEAS-2B cell line; the cell line thus derived is BZR. This cell line has been shown to be able to form tumors in nude mice with a latency period of two weeks, and is able to grow in an anchorage-independent fashion in soft agar.

(7) Use of cells altered by transfer of oncogenes as in paragraph 6 above to screen for potential chemotherapeutic agents (by the techniques described in paragraph 1 above) especially those which may be specific for cells transformed by the activation of particular oncogenes or combination of oncogenes.

(8) Studies of cellular biochemistry, including changes in intracellular pH and calcium levels, as correlated with cell growth and action of exogenous agents including but not limited to those described in paragraphs 1 through 7 above. To study intracellular pH and calcium levels, cells in suitable culture vessels are exposed to fluorescent indicator dyes and then fluorescence emissions are detected with a fluorescence spectrophotometer (Grynkiewicz et al., *J. Biol. Chem.* 260:3440-3450, 1985).

(9) Studies of cellular responses to growth factors and production of growth factors: Identification and purification of growth factors important for growth and differentiation of human bronchial epithelial cells. These cells are particularly useful for such an application since they grow in serum-free media. Therefore, responses to growth factors can be studied in precisely defined growth media and any factors produced by the cells may be identified and purified without the complication of the presence of serum.

(10) Use of recombinant DNA expression vectors to produce proteins of interest. For example, the gene encoding a protein of therapeutic value may be recombined with controlling DNA segments (i.e. containing a promoter with or without an enhancer sequence), transferred into the cell (e.g., by strontium phosphate transfection) and then the protein produced may be harvested from the culture supernatant or a cellular extract by routine procedures well known in the art.

(11) Studies of intracellular communication e.g., by dye scrape loading assays. To determine whether the cells growing in vitro have the ability to communicate via gap junctions, the cultures may be scraped, e.g., with a scalpel in the presence of a fluorescent dye in the growth medium. Cells at the edge of the wound are mechanically disrupted and therefore take up dye; whether intercellular communication has occurred may be ascertained by determining whether cells distant from the wound also contain dye.

(12) Characterization of cell surface antigens: The cells are incubated with an antibody against the cell surface antigen of interest, and then reacted with a second antibody which is conjugated to a fluorescent dye. The cells are then evaluated using a fluorescence activated cell sorter to determine whether they are fluorescent and therefore possess the cell surface antigen.

(13) hybrid studies for identification of tumor suppressor activity (Stanbridge et al., *Science* 215:252-259, 1982). To determine whether these cell lines contain tumor suppressor genes, they are fused to malignant tumor cells. The presence of tumor suppressor genes is indicated by loss of malignancy e.g., as detected by loss of ability to form tumors in athymic nude mice, in the hybrid cells.

(14) Identification of novel genes, including transforming genes in naturally concurring cancers described in paragraph 6 above, growth factor genes as described in paragraph 9 above, tumor suppressor genes as described in paragraph 13 above, using standard molecular biological techniques (Davis et al., *Methods in Molecular Biology*, New York: Elsevier, 1986) and techniques such as cDNA subtraction cloning and the like.

Of course, a kit for screening carcinogenic or antineoplastic agents and for any other usage as described herein supra, is easily assembled, comprising container(s) containing the cell line(s) of the present invention. Other components routinely found in such kits may also be included with instructions for performing the test.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. Non-tumorigenic, human bronchial epithelial or mesothelial cell line or derivative thereof growing without senescence when cultured in vitro in growth medium, said cell lines being selected from the group consisting of those having the identifying characteristics of ATCC CRL 9608, 9609, 9442, 9443, 9444, 9482 and 9483.

2. The cell of claim 1 having the identifying characteristics of ATCC CRL 9608.

3. The cell of claim 1 having the identifying characteristics of ATCC CRL 9609.

4. The cell of claim 1 having the identifying characteristics of ATCC CRL 9442.

5. The cell of claim 1 having the identifying characteristics of ATCC CRL 9443.

6. The cell of claim 1 having the identifying characteristics of ATCC CRL 9444.

7. The cell of claim 1 having the identifying characteristics of ATCC CRL 9482.

8. The cell of claim 1 having the identifying characteristics of ATCC CRL 9483.

9. The cell of claim 1 further comprising an oncogene.

10. A kit for screening carcinogenic or chemotherapeutic agent comprising a container containing a nontumorigenic, human bronchial epithelial or mesothelial cell line or derivative thereof according to claim 1 growing without senescence when cultured in vitro in growth medium.

11. A method for testing carcinogenicity of an agent, comprising culturing the cell line of claim 1 with an agent suspected of being carcinogenic and determining formation of abnormal cellular mass by said cell line, the formation of abnormal cellular mass being indicative of carcinogenicity of said agent.

12. A method for testing antineoplastic activity of an agent, comprising culturing the cell line of claim 1 with a potential antineoplastio agent and determining growth of said cell line, a lack of growth of said cell line being indicative of antineoplastic potency of said agent.

* * * * *